United States Patent
Baumbach et al.

[11] Patent Number: 5,257,835
[45] Date of Patent: Nov. 2, 1993

[54] ARRANGEMENT FOR CONNECTING TWO SECTIONS OF A FLUID SYSTEM

[75] Inventors: Frank Baumbach, Rödermark; Horst Randhahn, Darmstadt-Eberstadt; Ulrich Otto, Mühlheim, all of Fed. Rep. of Germany

[73] Assignee: Pall Corporation, Glen Cove, N.Y.

[21] Appl. No.: 811,680

[22] Filed: Dec. 23, 1991

[30] Foreign Application Priority Data

Dec. 24, 1990 [EP] European Pat. Off. ........ 90125453.2

[51] Int. Cl.$^5$ .............................................. F16I 19/00
[52] U.S. Cl. ..................... 285/330; 285/110; 285/924
[58] Field of Search ................. 285/13, 14, 330, 924, 285/110

[56] References Cited

U.S. PATENT DOCUMENTS

| | | | |
|---|---|---|---|
| 907,187 | 12/1908 | Sheckler | 285/14 |
| 1,774,631 | 9/1930 | Boosey | 285/332.4 X |
| 2,906,548 | 9/1959 | Faccou | 285/14 |
| 2,967,068 | 1/1961 | Gressel | 285/14 X |
| 3,499,461 | 3/1970 | Tuma | 137/240 |
| 3,672,704 | 6/1972 | Christianson | 285/334.4 X |
| 4,623,123 | 11/1986 | Traylor | 285/14 X |
| 4,711,471 | 12/1987 | Pallini, Jr. et al. | 285/305 X |

FOREIGN PATENT DOCUMENTS 8300812 3/1983 PCT Int'l Appl.
480581 12/1969 Switzerland.

OTHER PUBLICATIONS

"Die neue Aseptik Ventil Generation", Hermetisch Dichtend et al.
"Aseptik Rohrverbindungen". SUDMO 2 pages.

Primary Examiner—Richard E. Moore
Attorney, Agent, or Firm—Leydig, Voit & Mayer

[57] ABSTRACT

An arrangement for connecting two parts of a fluid system, preferably an aseptic system, by which the pressure gradient acts from the outside to the inside. The one system part carries an O-ring in a groove open to the other system part and open radially outwardly and the other system part is pressed against the O-ring by an axial holding device. To avoid dead space, in which bacteria could deposit, a space formed by the O-ring, the two system parts and the axial holding device is provided with a communication to the surroundings.

16 Claims, 1 Drawing Sheet

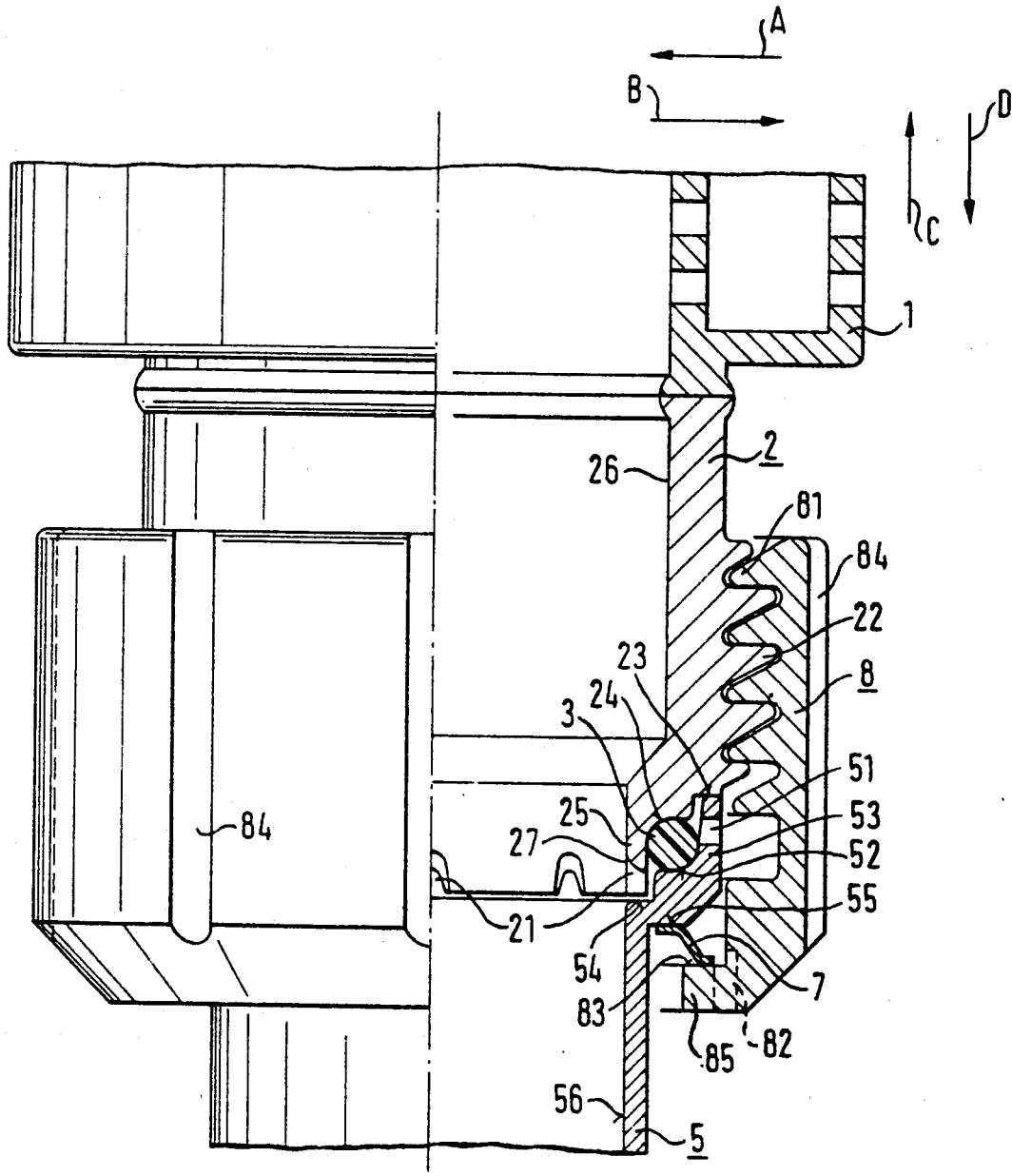

ARRANGEMENT FOR CONNECTING TWO SECTIONS OF A FLUID SYSTEM

The invention relates to an arrangement for connecting two sections of a fluid system, preferably an aseptic system.

An aseptic screw connection with O-ring is known (RA 2287 produced by SÜDMO-Amaturenfabrik GmbH, Germany) by which two pipe sections are connected by means of a union nut. Each pipe section has an inner circumferential groove shaped as a quarter of a circle up to a semicircle, so that in the screw-connected condition of the two pipe sections, an O-ring is compressed into the space formed by the two grooves, so that the inside diameter of the O-ring tightly closes with the inside diameters of the two pipe sections. This aseptic connection is suited for applications in which a differential pressure acts from the inside to the outside, i.e. the pressure in the interior of the pipe connection is larger than the outside pressure. In the sealing region of this aseptic connection, no gaps or hollow spaces are present in which bacteria could deposit over longer periods.

An aseptic adaptor of Pall Corporation is also known for connecting a filter element with a pipe section (double O-ring adaptor, Code 7, Pall Corporation) by which a spigot of the filter element has a protrusion for a bayonet closing means as well as two radially outer grooves at the end of the spigot, which each are suited for accepting one O-ring respectively. The pipe section to be connected to the spigot has a bayonet element as well as a portion which lies opposed to the openings of the two grooves in the spigot in the closed condition and which compress the two O-rings. The construction is such that the inner diameter of the spigot and the inner diameter of the pipe section are approximately the same and only a small gap remains between the two elements in the connected condition. This arrangement is suited for applications by which the differential pressure acts from the outside to the inside, i.e. the pressure in the interior of the adaptor is smaller than the outside pressure. This arrangement has the drawback that a gap is located above the O-rings which can not be emptied, i.e. drained, and that a closed space arises between the two O-rings, which is not reached by sterilization steam.

The object of the present invention is to provide an arrangement for gas or liquid connections of two tube-like system parts, where dead spaces are avoided and the differential pressure acts from the outside to the inside.

In accordance with the present invention, an arrangement for connecting two parts of a fluid system is provided as defined in the claims. The adaptor arrangement according to the invention is preferably employed for gas or liquid connections of system parts of an aseptic system. To guarantee a sealing which is free of dead spaces and safe from bacteria, it is necessary that the O-ring always be compressed (also during a sterilization procedure) and that condensation on both sides of the seal can run-off. Dead space is to be understood in this conjunction as a space in which a fluid, for example condensation, can remain over a longer time during normal operation of the adaptor arrangement. The danger arises that bacteria become deposited in such dead spaces, and that they also withstand a sterilization procedure.

The arrangement of the present invention is preferably used when the external pressure is larger than the pressure in the interior of the arrangement. By providing the communication of a space, formed by the O-ring the two parts of the system and the axial holding means, with the surroundings, this space is accessible when sterilizing, so that no bacteria can build up there.

It is preferred that the O-ring be radially stretched. This, for example, prevents the O-ring from releasing when connecting the system parts or taking on an improper position when the connection is made.

In a further preferred embodiment, one of the system parts has an outer shoulder, which serves as a contact surface for a rim portion or a protruding crown portion of the other part of the system. The tolerances in manufacture of the parts is preferably such that the O-ring is compressed into the ideal elastic region when the shoulder and the rim or ridge portion contact one another.

To provide favorable flow conditions in the interior of the arrangement, the one part of the system can have the same inside diameter as the other, at least in its region adjacent to the other part of the system. The regions of the first part of the system not adjacent to the second system part can have any inside diameter. The transition between the two regions should be gradual. Furthermore, the gap between the two parts of the system can be made as small as possible, so that laminar flow in the interior is disturbed as little as possible.

In a further preferred embodiment, the one part of the system is generally arranged above the other part of the system. Means for avoiding dead spaces are then preferably provided so that a liquid in existing gaps or spaces can flow off downwardly due to gravity. Thus, the upper system part has recesses about the circumference of its leading edge, which support drainage from the inner gap between the system parts and is so constructed that the flow in the interior of the arrangement is disturbed as little as possible. This can for example be achieved in that the cross-section of the recesses are tapered from the inside to the outside, preferably with a hyperbolic or a parabolic form. The rim portion of the lower system part protruding upwardly to contact with the shoulder of the upper system part is preferably provided with radial openings at about the height of the O-ring, which allow flow off from the outer space between the two system parts and the O-ring. The axis of the openings can preferably also be inclined to further promote this function.

The axial holding means are preferably provided as a union nut with saw-tooth threading. The saw-tooth threading is directed such that a radial expansion of the elements provided with saw teeth, for example at elevated temperatures during sterilization, is possible without altering the sealing properties, i.e. the inter-related positioning of the system parts. A spring washer guarantees that the system parts do not retract from one another to the extent that the seal is broken.

The spring washer preferably has a cross-section such that condensation fluid can flow off downwardly at an angle and in the region of the contact surface, openings are provided in the union nut in the area of the radially outward most end of the spring washer, so that the condensation fluid flowing off of the spring washer can flow out of the space between the union nut and the system parts.

Further advantageous, features and applications of the present invention are described in the following description of an embodiment in conjunction with the drawing.

The FIGURE shows a partial cross-section of an embodiment of the adaptor of the invention.

The figure shows a filter element of 1, a threaded adaptor 2 as one part of the system, an O-ring 3, a housing adaptor 5 as another part of the system, a spring washer 7 and a union nut 8.

The arrows A, B, C, D define directions used in the following, where A points to the inside and B to the outside (holds only for the right half of the figure). The arrows C and D indicate longitudinal directions, C an upward direction and D a downward direction.

The threaded adaptor 2 is attached to the filter element 1, namely by welding, adhering, etc. The threaded adaptor 2 has an upper portion 26 with a larger inside diameter and a lower portion 27 with a smaller diameter. The inside diameter of the lower portion 27 corresponds to the inside diameter of the housing adaptor 5. The transition from the upper portion 26 to the lower portion 27 is gradual.

The threaded adaptor 2 has a saw-tooth outer threading 22, whose inclined surfaces run from the lower inside to the upper outside. A shoulder 23 exposed to the outside is provided below the outer threading 22 and positioned slightly to the inside. A groove 24, half open to the outside, is provided between the shoulder 23 and the lower end of the threaded adaptor 2 for receiving the O-ring. An inner ridge portion 25 of the groove 24 is provided with recesses at spacings about its circumference, which for example can be V shaped and which normally extend upwardly to about the level of the O-ring 3, which however are not in contact with same. The form of the recesses 21 is such that the inner length of the recesses is larger than the outer length, so that no edges causing flow disturbance are formed on the inner wall of the portion 27. The valley of the groove 24 is formed corresponding to the form of the O-ring 3, i.e. a circular valley whose radius corresponds to the radius of the O-ring 3. The outer diameter of the threaded adaptor 2 is dimensioned in the region of the O-ring 3 so that the O-ring is under tension when mounted on the threaded adaptor 2. The tension lies in the range of 1 to 5%, preferably about 2%.

The housing adaptor 5 as seen from bottom to top, initially has a smooth section with an interior surface 56, whose inside diameter corresponds to the inside diameter of the portion 27. A shoulder 54 open to the inside then follows, whose extension in transverse direction is somewhat broader than the ridge portion 25 of the threaded adaptor 2. A groove 52 half open to the inside follows the shoulder 54 after a short longitudinal portion. The valley region of the groove corresponds to that of the O-ring 3, similar to the valley of the groove 24. An outer ridge 53 forms the upper end of the housing adaptor 5 and extends in the longitudinal direction to the shoulder 23. The shoulder 23 forms a contact or stop for the housing adaptor 5. The ridge 53 is provided with bores 51 arranged transversely or inclined upwardly (seen from the outside to the inside), whose lowest portion lies at the height of the upper half of the O-ring 3, preferably near the center of the O-ring 3 and which provides run-off of the medium (fluid). A counter surface 55 lying perpendicular to the center axis of the arrangement is provided on the outer surface of the housing adaptor 5.

The union 8 has a saw-tooth inner threading 81, corresponding to the outer threading 22 of the threaded adaptor 2, a transverse, inner contact surface 83 arranged so that the spring washer 7 engages between the countersurface 55 and the contact surface 83, and is provided on its outer circumference with longitudinal grooves 84, into which a suitable tool can be applied for rotating the nut 8. This has the advantage over a hexagon nut, that the nut 8 can be drawn down when limited space is available, also when several elements are involved. On its inner circumference, the union 8 below the saw-tooth threading 81 is configured such that it does not contact the housing adaptor 5, so that the region with threads can drain off. An end section 85 of the union nut 8 is provided with several axial run-off holes 82, which are arranged such that they avoid the spring washer 7 and provide a communication between the surroundings and the space formed between the union nut 8, the spring washer 7, the threaded adaptor 2 and the housing adaptor 5.

When assembling the aseptic system comprising two parts, the O-ring 3 is first mounted under radial tension as described before in the groove 24. The radial tension prevents the O-ring 3 from slipping off of the threaded adaptor 2, for example by gravity. The housing adaptor 5 with the union nut 8 and the spring washer 7 is then mounted to the threaded adaptor 2 from the bottom and screwed together with same. The union nut is drawn down until contact is made between the shoulder 23 and the ridge 53. The components are fabricated to such an accuracy, that the O-ring 3 operates in the ideal elastic range between 10 and 25% compression when the nut is screwed down to the contact. The screw connection guarantees that the adaptor elements 2 and 5 never retract from one another so far that the seal is no longer tight. The spring washer 7 contributes substantially to the fact that the screw connection, which provides the compression, does not release. The provision of the threading with a saw-tooth profile provides that the sealing characteristic remains constant, even when he threaded adaptor 2, which normally is made of synthetic material, expands radially for example when the temperature increases during sterilization. It is clear that the transverse sections of the saw-tooth profile are responsible for the axial tension effect and not the inclined sections.

The reduction or elimination of dead space in the interior of the adaptor arrangement rests on the condition that the fluid flow in the interior should be free of disturbance as far as possible. For this purpose, the threaded adaptor 2 is configured with an inside diameter of its lower portion 27 which corresponds to the inside diameter of the housing adaptor 5 and in the screwed down state of the adaptor arrangement (down to the contact or stop), only a small gap remains between the two adaptor elements 2 and 5. Despite this, to still avoid dead space, the threaded adaptor 2 is provided with V-shaped recesses 21 about the circumference of the ridge section 25. Condensation formed in the region of the O-ring 3 between the ridge or rim portion 25 and the shoulder 54 can therefore flow off via the recesses 21. The recesses 21 are formed to provide flow-off, where the length of the recess in the longitudinal direction on the inside is larger than on the outside with a gradual transition.

The danger of having dead space in the region between the O-ring 3, the threaded adaptor 2 and the housing adaptor 5 is excluded in that the housing adaptor 5 is provided with run-off or drainage bores 51 in the ridge 53, which are arranged such that a fluid, for example condensation water, can flow out of the mentioned region. As can be seen from the drawing the arrangement of the adaptor components in this region is provided for the vertical arrangement (threaded adaptor above the housing adaptor) so that the condensation can flow off simply by means of gravity.

In the space formed between the threaded adaptor 2, the housing adaptor 5, the spring washer 7 and the union nut 8, dead space is avoided by the run-off holes 82 and the union nut 8, where the design of all adaptor components here is also such that any fluid in the space can flow off simply by gravity. For example, the spring washer 7 is formed so that fluid flows off in an inclined manner.

| List of Reference Numerals | |
|---|---|
| 1 | Filter element |
| 2 | Threaded adaptor |
| 3 | O-ring |
| 5 | Housing adaptor |
| 7 | Spring washer |
| 21 | Recesses |
| 22 | Saw-tooth outer threading |
| 23 | Shoulder |
| 24 | Groove |
| 25 | Ridge |
| 26 | Upper portion |
| 27 | Lower portion |
| 51 | Drainage bore |
| 52 | Groove |
| 53 | Ridge |
| 54 | Shoulder |
| 55 | Counter surface |
| 56 | Interior surface |
| 81 | Saw-tooth inner threading |
| 82 | Run-off hole |
| 83 | Contact surface |
| 84 | Longitudinal grooves |
| 85 | End section |

We claim:

1. An arrangement for a fluid system comprising: first and second system parts, the first system part having a groove which opens to the second system part and which opens radially outwardly and having a saw-tooth outer threading and the second system part having a countersurface; an O-ring disposed in the groove of the first system part; and an axial holding device arranged to press the O-ring against the second system part, the axial holding device including a union nut having a saw-tooth inner threading and a contact surface and further including a spring washer which engages the contact surface of the union nut and the countersurface of the second system part, wherein a space is provided between the O-ring, the two system parts, and the axial holding device which is open to the surroundings.

2. The arrangement of claim 1, wherein the union nut comprises at least one approximately axial hole in the region of the contact surface.

3. An arrangement for a fluid system comprising: first and second system parts, wherein the first system part has a groove which opens to the second system part and which opens radially outwardly and further has an outer radial shoulder and wherein the second system part has a groove which opens to the first system part and which opens radially inwardly and further has an outer ridge portion; an O-ring disposed in the grooves of the first and second system parts and elastically stretched in the range from 1% to 5%; and an axial holding device arranged to press the O-ring between the first and second system parts and compress the O-ring within the ideal elastic range, the outer radial shoulder of the first system part serving as a stop for the outer ridge portion of the second system part, wherein a space is provided between the O-ring, the two system parts, and the axial holding device, which is open to the surroundings.

4. An arrangement for a fluid system comprising: a seal including an O-ring; a first system part defining an interior channel and including a first groove, the O-ring being disposed in the first groove; a second system part defining an interior channel and including a second groove, the O-ring being disposed in the second groove; and an axial holding device arranged to couple the first and second system parts in abutting engagement with the interior channel of the first system part communicating with the interior channel of the second system part and the O-ring compressed between the first and second system parts, wherein the O-ring, the two system parts, and the axial holding device define a space therebetween which is open to the surroundings.

5. The arrangement of claim 4 wherein the O-ring is elastically stretched in the range from 1% to 5%.

6. The arrangement of claim 4 wherein the first system part further includes a shoulder and the second system part further includes a ridge adapted to abut the shoulder and compress the O-ring within an ideal elastic range.

7. The arrangement of claim 6 wherein the ridge includes a bore.

8. The arrangement of claim 4 wherein the O-ring and the two system parts define therebetween a second space which communicates with the interior channels of the first and second system parts.

9. The arrangement of claim 4 wherein the first system part further includes a ridge and at least a portion of the interior channel of the first system part is defined by an inner surface of the ridge and wherein the interior channel of the second system part is defined by an inner surface which is flush with the inner surface of the ridge of the first system part.

10. The arrangement of claim 9 wherein the ridge includes at least one recess.

11. The arrangement of claim 4 wherein the axial holding device includes a union nut surrounding the first and second system parts.

12. The arrangement of claim 11 wherein the first system part includes a saw-tooth outer thread and wherein the union nut includes a saw-tooth inner thread.

13. The arrangement of claim 12 wherein the second system part includes a countersurface, wherein the union nut includes a contact surface, and wherein the axial holding device further includes a spring washer positioned between the countersurface and the contact surface.

14. The arrangement of claim 13 wherein the union nut has a hole in the vicinity of the contact surface.

15. The arrangement of claim 4 wherein the groove of the first system part opens radially outwardly and the O-ring is disposed in the groove and elastically stretched in the range from 1% to 5%, the first system part further including a shoulder disposed radially outwardly from the O-ring and a ridge disposed radially inwardly from the O-ring and having at least one recess and an inner surface which defines at least a portion of the interior channel of the first system part; wherein the groove of the second system part opens radially inwardly and the interior channel of the second system part is defined by an inner surface which is flush with the inner surface of the ridge of the first system part, the first system part further including a ridge disposed radially outwardly from the O-ring and having a length which is greater than the diameter of the O-ring, the ridge of the second system part having a substantially radial bore and being adapted to abut the shoulder of the first system part and compress the O-ring within an ideal elastic range; and wherein the two system parts and the O-ring define therebetween a second space which communicates with the interior channels of the two system parts.

16. The arrangement of claim 15 wherein the first system part includes a saw-tooth outer thread, wherein the second system part includes a countersurface, and wherein the axial holding device includes a union nut surrounding the first and second system parts and having a saw-tooth inner thread and a generally axial hole in the vicinity of the contact surface, the axial holding device further including a spring washer positioned between the contact surface of the union nut and the countersurface of the second system part.

* * * * *